United States Patent
Loy et al.

(10) Patent No.: US 9,814,659 B2
(45) Date of Patent: Nov. 14, 2017

(54) METHODS OF LIGHTENING THE SKIN

(75) Inventors: Chong Jin Loy, Singapore (SG);
Khalid Mahmood, South Hadley, MA (US); Claude Saliou, Basking Ridge, NJ (US); Paul Warren Reddell, Yungaburra (AU); Victoria Anne Gordon, Yungaburra (AU)

(73) Assignee: Johnson & Johnson Consumer Inc., Skillman, NJ (US)

(*) Notice: Subject to any disclaimer, the term of this patent is extended or adjusted under 35 U.S.C. 154(b) by 0 days.

(21) Appl. No.: 13/437,298

(22) Filed: Apr. 2, 2012

(65) Prior Publication Data
US 2013/0259815 A1  Oct. 3, 2013

(51) Int. Cl.
| *A61K 8/36* | (2006.01) |
| *A61Q 19/02* | (2006.01) |
| *A61K 8/97* | (2017.01) |
| *A61K 8/02* | (2006.01) |

(52) U.S. Cl.
CPC .............. *A61K 8/36* (2013.01); *A61K 8/0212* (2013.01); *A61K 8/97* (2013.01); *A61Q 19/02* (2013.01)

(58) Field of Classification Search
CPC combination set(s) only.
See application file for complete search history.

(56) References Cited

U.S. PATENT DOCUMENTS

| 4,939,171 A * | 7/1990 | Moeller et al. ............... 514/530 |
| 7,442,391 B2 | 10/2008 | Koganov |
| 7,473,435 B2 | 1/2009 | Kogavov |
| 7,537,791 B2 | 5/2009 | Koganov |
| 2005/0226834 A1 | 10/2005 | Lambino et al. |
| 2009/0241242 A1 | 10/2009 | Beatty et al. |
| 2011/0318439 A1 * | 12/2011 | Gordon et al. ............... 424/777 |

FOREIGN PATENT DOCUMENTS

| CN | 102307842 A | 1/2012 |
| JP | 2005132793 A | 5/2005 |
| JP | 2009013128 | 1/2009 |
| JP | 2009013128 A * | 1/2009 |
| JP | 2010106000 A | 5/2010 |
| WO | WO 2010/111745 A1 | 10/2010 |

OTHER PUBLICATIONS

SkinlightCo.uk: "Skin Brightening Fruit Fiesta Peel," (URL:http://www.skinlight.co.uk/product_845_Skin+Brightening+Fruit+Fiesta+Peel+.html—Jan. 1, 2006).*
Colipa Guideline: Guideline for the Colorimetric Determination of Skin Colour Typing and Prediction of the Minimal Erythema! Dose (MED) Without UV Exposure (2007).
De Silva et al., "Demethylacrovestone From Achronychia Pedunculata Fruits", Phytochemistry, (1991), 30(5), pp. 1709-1710.
EP Search Report for Application No. EP 13 16 1759 dated Nov. 19, 2015.
Mintel—Fruit Fiesta Peel, MyChelle Dermaceuticals Age Defense, Apr. 2012.
Shinichi et al., "Synthesis and Cosmetic Whitening Effect of Glycosides Derived from Several Phenylpropanoids", Yakugaku Zasshi=Journal of the Pharmaceutical Society of Japan, JP, vol. 126, No. 3, Mar. 1, 2006, pp. 173-177, XP009081014, ISSN: 0031-6903, DOI: 10 1248/Yakushi. 126.173.
Solano et al., "Hypopigmenting Agents: an updated review on biological, chemical and clinical aspects", Pigment Cell Research, vol. 19, No. 6, Dec. 1, 2006, pp. 550-571, XP0906-9305, ISSN: 0906-9305 DOI: 10.1111/J.1600-0749.2006.00334.X; Retrieved from the Internet: URL:http://leenyx.icecreamlovestheweb.com/backend/media/54201093909AM/Hypopigmenting%20agents%20an%20Oupdated%20review%20on.pdf [retrieved on Aug. 8, 2006].
Su et al., " Acetophenone Derivatives from Acronychia pedunculata", Journal of Natural Products, (2003), 66(7) pp. 990-993.
Zuo, Xialin et al., the 11th Southeast Asia Cosmetic Medicine Academic Conference, p. 29-31, Dec. 31, 2009—No translation—See CN Office Action.
Zuo, Xialin et al., the 11th Southeast Asia Cosmetic Medicine Academic Conference, p. 29-32, Dec. 31, 2009—No translation—See CN Office Action.

* cited by examiner

*Primary Examiner* — Robert Cabral

(57) ABSTRACT

Provided are methods of lightening skin by applying certain aromatic compounds or botanical extracts containing such compounds to the skin.

19 Claims, No Drawings

METHODS OF LIGHTENING THE SKIN

FIELD OF INVENTION

The present invention relates to methods of lightening skin by applying certain aromatic compounds or botanical extracts containing such compounds to the skin.

DESCRIPTION OF RELATED ART

A variety of aromatic compounds have been identified and used on skin to provide a variety of personal care benefits. For example, U.S. Pat. No. 4,939,171 assigned to Henkel discloses the use of compounds including 3-(4-farnesyloxyphenyl)-propionic acid to provide antiseborrhoeic properties. The patent does not, however, identify any skin lightening properties associated with the compositions therein.

In addition, U.S. Patent Application No. 2011/0318439 assigned to Ecobiotics LTD., discloses compounds derived from botanicals of the genus *Acronychia*, including 3-(4-farnesyloxyphenyl)-propionic acid, for use as antioxidants, antibacterials, anthelmintics, anti-inflammatories, cancer chemopreventatives, food additives and/or fragrances components. The patent does not, however, identify any skin lightening properties associated with the compositions therein.

Moreover, applicants have recognized that the identification of other benefits is not a predictor of skin lightening benefits. For example, several antioxidants have been reported to darken the skin by inducing melanin, see for example, Solano et al. Pigment Cell Res. 2006, 19 (550-571).

The present invention is directed to the discovery that certain aromatic compounds and/or botanical extracts containing such molecules exhibit unexpected combinations of skin lightening, low cytotoxicity, photo-protective, and/or other consumer-desirable properties for use on skin.

SUMMARY OF THE INVENTION

Applicants have discovered unexpectedly that certain aromatic compounds, in particular, compounds of Formula I below, and botanical extracts containing such compounds, including plants of the genus *Acronychia*, may be used on skin to provide significant skin lightening or a combination of skin lightening with photo-protectivity and/or relatively low cytotoxicity.

Accordingly, in one aspect, the present invention is directed to methods of lightening skin comprising applying to skin in need of skin lightening a compound of Formula I:

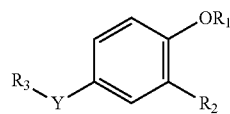

(I)

wherein:

$R_1$ is selected from the group consisting of $C_1$-$C_{20}$ alkyl, $C_2$-$C_{20}$ alkenyl, $C_2$-$C_{20}$ alkynyl, and $C_3$-$C_8$ cycloalkyl or aryl;

$R_2$ is selected from the group consisting of hydrogen, hydroxyl, $C_1$-$C_6$ alkyl, $C_2$-$C_6$ alkenyl, $C_2$-$C_6$ alkynyl, $C_3$-$C_8$ cycloalkyl or aryl, —$OC_1$-$C_6$ alkyl, —$OC_2$-$C_6$ alkenyl, —$OC_2$-$C_6$ alkynyl, —$OC_3$-$C_8$ cycloalkyl or aryl, thiol, —$SC_1$-$C_6$ alkyl, —$SC_2$-$C_6$ alkenyl, —$SC_2$-$C_6$ alkynyl, —$SC_3$-$C_8$ cycloalkyl or aryl, —$NR_4C_1$-$C_6$ alkyl, —$NR_4C_2$-$C_6$ alkenyl, —$NR_4C_2$-$C_6$ alkynyl, and —$NR_4C_3$-$C_8$ cycloalkyl or aryl;

$R_3$ is selected from —$CO_2H$, —$CO_2R_4$ or an isosteric equivalent of a carboxy group, wherein $R_4$ is $C_1$-$C_6$ alkyl, $C_2$-$C_6$ alkenyl, $C_3$-$C_8$ cycloalkyl or aryl; and Y is —($CH_2$—$CH_2$)—, —(CH=CH)—, or —(C≡C)—;

or a cosmetically acceptable salt thereof.

DESCRIPTION OF THE INVENTION

All percentages listed in this specification are percentages of active/solids material by weight, unless otherwise specifically mentioned.

As used herein, the term "lightening skin" refers generally to lightening, brightening, whitening, and/or evening of the skin tone, skin color, and/or shade of skin, and/or to the reduction in sallowness, and/or to the lightening and/or fading of hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In certain embodiments, "lightening the skin" also refers to increased skin radiance, glow, translucency and/or luminescence and/or obtaining a more radiant, glowing, translucent or luminous skin tone appearance or a less yellow or sallow skin tone. In certain preferred embodiments, "lightening the skin" refers to lightening the skin tone, evening the skin tone, increasing skin radiance, lightening age spots.

As used herein, the term "skin in need of skin lightening treatment" refers generally to skin that exhibits one or more property selected from the group consisting of: skin having a measured Individual Typology Angle (ITA) value below 41 as determined per the COLIPA GUIDELINE: GUIDELINE FOR THE COLORIMETRIC DETERMINATION OF SKIN COLOUR TYPING AND PREDICTION OF THE MINIMAL ERYTHEMAL DOSE (MED) WITHOUT UV EXPOSURE published in 2007, which is incorporated herein by reference and further described below, darkened and/or sallow skin, including skin darkened by ultraviolet rays (UV), skin with uneven skin tone, or skin with one or more hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In the COLIPA guidelines, skin color is defined function of the ITA value as: very light skin>55; Light skin 41-55, Intermediate 28-41, and Tan skin<28. In certain preferred embodiments, "skin in need of skin lightening" refers to individuals with a skin having an ITA value of less than 41, such as about 40 or less, about 35 or less, about 30 or less, or more preferably about 28 or less. In certain other preferred embodiments, the present invention is directed to compositions and methods for use on skin in need of skin lightening treatment selected from sallow and/or darkened skin, including skin darkened by UV. In certain preferred embodiments, the skin in need of skin lightening is skin having an uneven skin tone. In certain other preferred embodiments, the present invention is directed to compositions and methods for use on skin in need of skin lightening treatment selected from the group consisting of age spots, freckles, marks left after acne, and combinations of two or more thereof.

As used herein, a composition that is "essentially free" of an ingredient means the composition that has about 2% or less of that ingredient by weight based on the total weight of the composition. Preferably, a composition that is essentially free of an ingredient has about 1% or less, more preferably about 0.5% or less, more preferably about 0.1% or less, more preferably about 0.05 or less, more preferably about 0.01% or less by weight based on the total weight of composition of the ingredient. In certain more preferred embodiments, a composition that is essentially free of an ingredient is free of the ingredient, i.e. has none of that ingredient in the composition.

As used herein, "cosmetically/dermatologically acceptable" means that the ingredients which the term describes are suitable for use in contact with tissues (e.g., the skin or hair) without undue toxicity, incompatibility, instability, irritation, allergic response, and the like. As will be recognized by one of skill in the art, a cosmetically-acceptable salt of a compound of Formula I herein may include base addition salts which are formed with organic or inorganic bases. Acceptable salts from inorganic bases include, for example, sodium or potassium salts, and the like. Acceptable salts from organic bases include, for example, salts formed with primary, secondary, or tertiary amines, and the like.

As used herein, the term "safe and effective amount" means an amount of the extract or of the composition sufficient to induce the desired effect, but low enough to avoid serious side effects. The safe and effective amount of the compound, extract, or composition will vary with e.g. the age, health and environmental exposure of the end user, the duration and nature of the treatment, the specific extract, ingredient, or composition employed, the particular pharmaceutically-acceptable carrier utilized, and like factors.

According to the present invention, methods of lightening the skin comprise applying to the skin a compound of Formula I:

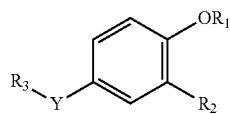
(I)

wherein:

$R_1$ is selected from the group consisting of $C_1$-$C_{20}$ alkyl, $C_2$-$C_{20}$ alkenyl, $C_2$-$C_{20}$ alkynyl, and $C_3$-$C_8$ cycloalkyl or aryl;

$R_2$ is selected from the group consisting of hydrogen, hydroxyl, $C_1$-$C_6$ alkyl, $C_2$-$C_6$ alkenyl, $C_2$-$C_6$ alkynyl, $C_3$-$C_8$ cycloalkyl or aryl, —$OC_1$-$C_6$ alkyl, —$OC_2$-$C_6$ alkenyl, —$OC_2$-$C_6$ alkynyl, —$OC_3$-$C_8$ cycloalkyl or aryl, thiol, —$SC_1$-$C_6$ alkyl, —$SC_2$-$C_6$ alkenyl, —$SC_2$-$C_6$ alkynyl, —$SC_3$-$C_8$ cycloalkyl or aryl, —$NR_4C_1$-$C_6$ alkyl, —$NR_4C_2$-$C_6$ alkenyl, —$NR_4C_2$-$C_6$ alkynyl, and —$NR_4C_3$-$C_8$ cycloalkyl or aryl;

$R_3$ is selected from —$CO_2H$, —$CO_2R_4$ or an isosteric equivalent of a carboxy group, wherein $R_4$ is $C_1$-$C_6$ alkyl, $C_2$-$C_6$ alkenyl, $C_3$-$C_8$ cycloalkyl or aryl; and Y is —($CH_2$—$CH_2$)—, —(CH=CH)—, or —(C≡C)—;

or a cosmetically acceptable salt thereof. In certain preferred embodiments, the method comprises applying to the skin a compound of Formula I wherein:

$R_1$ is selected from the group consisting of $C_5$-$C_{16}$ alkyl, $C_5$-$C_{16}$ alkenyl, and $C_5$-$C_{16}$ alkynyl, more preferably $C_5$-$C_{16}$ alkenyl, including, for example, farnesyl;

$R_2$ is selected from the group consisting of hydrogen, hydroxyl, —$OC_1$-$C_6$ alkyl, —$OC_2$-$C_6$ alkenyl, —$OC_2$-$C_6$ alkynyl, —$OC_3$-$C_8$ cycloalkyl, more preferably hydrogen, hydroxyl, —$OC_1$-$C_6$ alkyl, even more preferably hydrogen or —$OC_1$-$C_3$ alkyl;

$R_3$ is selected from —$CO_2H$, —$CO_2R_4$ wherein $R_4$ is $C_1$-$C_6$ alkyl, or an isosteric equivalent of a carboxy group; and Y is —($CH_2$—$CH_2$)— or —(CH=CH)—;

or a cosmetically-acceptable salt thereof. In certain preferred embodiments, the compounds of Formula I as acid or as alkylester form are selected from the group consisting of 3-(4-farnesyloxyphenyl)-propionic acid, 3-(4-farnesyloxy-3-hydroxyphenyl)-propionic acid, 3-(4-farnesyloxy-3-methoxyphenyl)-propionic acid, alkylesters thereof, in particular ethyl esters thereof, and combinations of two or more thereof. In certain more preferred embodiments, the methods of the present invention comprise applying 3-(4-farnesyloxyphenyl)-propionic acid or an ethyl ester thereof to skin in need of skin lightening, most preferably applying 3-(4-farnesyloxyphenyl)-propionic acid to skin in need of skin lightening.

Preferably, the methods of the present invention comprise applying a skin lightening effective amount of compound of Formula I to the skin, preferably a safe and effective amount. In certain preferred embodiments, the methods comprise applying from greater than zero to about 20% compound of Formula I to the skin in need. In certain other preferred embodiments, the methods comprise applying from about 0.0001 to about 20%, from about 0.001 to about 10%, from about 0.01 to about 5%, from about 0.1 to about 5%, or from about 0.2 to about 2% compound of Formula I to the skin in need. In certain other preferred embodiments, the methods comprise from greater than zero to about 1%, from about 0.0001 to about 1%, from about 0.001 to about 1%, or from about 0.01 to about 1% compound of Formula I to the skin.

The compounds of Formula I may be derived from any of a variety of natural sources, such as via extraction from botanicals, or may be synthesized using known synthetic methods. In certain preferred embodiments, the compounds of Formula I are extracted from botanicals including, for example, plants of the genus *Acronychia*, including, for example, from *Acronychia aberrans*, *Acronychia acidula*, *Acronychia acronychioides*, *Acronychia acuminate*, *Acronychia baeuerlenii*, *Acronychia chooreechillum*, *Acronychia crassipetala*, *Acronychia eungellensis*, *Acronychia imperforate*, *Acronychia laevis*, *Acronychia laurifolia*, *Acronychia littoralis*, *Acronychia oblongifolia*, *Acronychia octandra*, *Acronychia parviflora*, *Acronychia pauciflora*, *Acronychia pedunculata*, *Acronychia pubescens*, *Acronychia* species (Batavia Downs), *Acronychia suberosa*, *Acronychia vestita*, *Acronychia wilcoxiana*, and combinations of two or more thereof. In certain preferred embodiments, the extract is obtained from *Acronychia acidula*, *Acronychia aberrans*, *Acronychia acronychioides*, *Acronychia crassipetala*, or a combination of two or more thereof. In certain more preferred embodiments, the compound of Formula I is extracted from *Acronychia acidula*.

*Acronychia vestita*, *Acronychia pedunculata* and *Acronychia laurifolia* are reported to contain Acrovestone as a constituent thereof. Acrovestone is a prenylated acetophenone and additional analogs are reported from fruit and bark of plants from genus *Acronychia* specifically fruit extract of *Acronychia pedunculata* (Phytochemistry, (1991), 30(5), p 1709-10). Some anti-oxidant and anti-tyrosinase activities of acrovestone are reported (Journal of Natural Products, (2003), 66(7), p 990-3). In certain preferred embodiments, the extracts obtained from plants of *Acronychia* known to contain prenylated acetophenones are made free from acrovestone and its analogs or more generally free from prenylated acetophenones.

Any of a variety of extracts of *Acronychia* may be used for embodiments wherein the method comprises applying such an extract. The extract may be obtained from any part of the plant such as the fruit, the seed, the bark, the leaf, the flower, the roots and the wood. In certain preferred embodiments, the extract is obtained from the fruit of the plant. Suitable extracts of *Acronychia* fruit, seed, bark, leaves, flower, and wood may be obtained using conventional methods including, but not limited to, direct extraction of material from the biomass by grinding, macerating, pressing, squeezing, mashing, centrifuging, and/or processes such as cold percolation, agitation/distillation, microwave assisted extraction, supercritical/subcritical $CO_2$ compressed gas extraction with or without polar modifiers, pressurized solvent extraction, accelerated solvent extraction, pressurized or normal hot water extraction, surfactant assisted pressurized hot water extraction, oil extraction, membrane extraction, Soxhlet extraction, the gold finger distillation/extraction and/or processes disclosed, for example, in U.S. Pat. Nos. 7,442,391, 7,473,435, and 7,537,791 to Integrated Botanical Technologies, LLC, incorporated herein by reference, and the like, or by other methods such as solvent extraction, and the like. Any of a variety of solvents including polar solvents, non-polar solvents, or combinations of two or more thereof may be used in methods of comprising solvent extraction. Suitable polar solvents include polar inorganic solvents such as water and the like, polar organic solvents such as alcohols and corresponding organic acids, for example $C_1$-$C_8$ alcohols including methanol, ethanol, propanol, butanol, and the like and organic acids, including acetic acid, formic acid, propanoic acid, and the like, polyols and glycols, including $C_1$-$C_8$ polyols/glycols and the like, and combinations of two or more thereof. Suitable non-polar solvents include non-polar organic solvents such as alkanes, including $C_1$-$C_8$ alkanes, cycloalkanes, including $C_1$-$C_8$ alkanes, alkyl ethers, including $C_1$-$C_8$ alkyl ethers, Petroleum ethers, ketones, including $C_1$-$C_8$ ketones, methylene chloride, ethyl acetate, xylene, toluene, chloroform, vegetable oil, mineral oil and the like. In another embodiment extraction may be obtained by non-polar solvents described above or supercritical fluid extraction with or without a polar modifier such as $C_1$-$C_8$ alcohols, water, $C_1$-$C_8$ polyols/glycols or $C_1$-$C_8$ organic acids.

In certain other preferred embodiments, the extract of the invention comprises a combination of polar and non-polar extracts of from *Acronychia acidula* fruit.

In certain preferred embodiments, the extract of the invention comprises a polar extract prepared by extracting from fresh freeze dried fruits of *Acronychia acidula* using a polar solvent comprising water, $C_1$-$C_8$ alcohols, $C_1$-$C_8$ polyols, $C_1$-$C_8$ glycols, and combinations of two or more thereof. In certain more preferred embodiments, the extract is extracted using one or more $C_1$-$C_4$ alcohols, $C_1$-$C_4$ polyols, and/or $C_1$-$C_4$ glycols. In certain more preferred embodiments, the extract is prepared using a solvent comprising methanol, ethanol, or a combination thereof with or without presence of water. In more preferred embodiment, the extract is a polar extract extracted from *Acronychia acidula* fruit using a combination of alcohol and water.

In certain preferred embodiments, the extract comprises a non-polar extract prepared by extracting from *Acronychia acidula* fruit using a non-polar solvent comprising one or more $C_1$-$C_8$ alkanes, $C_1$-$C_8$ cycloalkanes, $C_1$-$C_8$ alkyl ethers, $C_1$-$C_8$ alkyl esters and/or chloroform, more preferably one or more $C_1$-$C_8$ alkanes, $C_1$-$C_8$ alkyl esters and/or chloroform. In certain more preferred embodiments, the non-polar extract is extracted from *Acronychia acidula* fruit using hexanes, ethyl acetate, chloroform or mixtures of two or more thereof. In even more preferred embodiments, the non-polar extract is extracted from *Acronychia acidula* fruit using ethyl acetate.

In certain embodiments, compounds of Formula I may be obtained via extraction of cell cultures of various plants, including cell cultures of plants of the genus *Acronychia*. The cell cultures which are extracted to obtain extracts/compounds of Formula I for use in the present invention may be of any form including suspension cell cultures and the like.

In certain embodiments, the method of the present invention comprises applying to skin in need of treatment, a composition comprising a botanical extract, wherein the extract comprises at least about 5% by weight of a compound of Formula I. In certain more preferred embodiments, the method comprises applying a composition comprising a botanical extract comprising at least about 20% by weight of compound of Formula I, for example at least about 40% by weight, at least about 50% by weight, at least 60% by weight, at least 70% by weight or at least 80% by weight of compound of Formula I. In certain embodiments, the methods of the present invention comprise applying to skin in need of treatment a composition comprising compound of Formula I that is isolated and/or purified to at least 90%. In certain preferred embodiments, the composition has incorporated or added thereto a compound of Formula I material that is greater than 90% pure compound of Formula I.

The extracts comprising compound of Formula I may be obtained by extraction from the whole plant or from a part of the plant, e.g. root, flower, fruit, leaves, stem, bark, or may be obtained from, fractions of materials derived from different botanicals or from different parts of the same botanical via any of the extraction methods as described herein. In certain embodiments, the extracts comprise a fraction, or a combination of two or more fractions, derived from one or more botanicals.

Any suitable carrier may be used in the compositions of the present invention. Preferably, for a skin care composition, the carrier is a cosmetically-acceptable carrier. As will be recognized by those of skill in the art, cosmetically-acceptable carriers comprise carriers that are suitable for use in contact with the body, in particular the skin for skin whitening applications, without undue toxicity, incompatibility, instability, irritation, allergic response, and the like. A safe and effective amount of carrier is from about 50% to about 99.999%, preferably from about 80% to about 99.9%, more preferably from about 99.9% to about 95%, most preferably from about 99.8% to about 98% of the composition. The carrier can be in a wide variety of forms. For example, emulsion carriers, including, but not limited to, oil-in-water, water-in-oil, water-in-oil-in-water, and oil-in-water-in-silicone emulsions, are useful herein. These emulsions can cover a broad range of viscosities, e.g, from about 100 cP to about 200,000 cP. Examples of suitable cosmetically-acceptable carriers include cosmetically-acceptable solvents and materials for cosmetic solutions, suspensions, lotions, creams, serums, essences, gels, toners, sticks, sprays, ointments, liquid washes and soap bars, shampoos, hair conditioners, pastes, foams, mousses, powders, shaving creams, wipes, patches, strips, powered patches, microneedle patches, bandages, hydrogels, film-forming products, facial and skin masks, make-up, liquid drops, and the like. These product types may contain several types of cosmetically-acceptable carriers including, but not limited to, solutions, suspensions, emulsions such as microemulsions and nanoemulsions, gels, solids, liposomes, other encapsulation technologies and the like.

The following are non-limitative examples of such carriers. Other carriers can be formulated by those of ordinary skill in the art. In one embodiment, the carrier contains water. In a further embodiment, the carrier may also contain one or more aqueous or organic solvents. Examples of organic solvents include, but are not limited to: dimethyl isosorbide; isopropylmyristate; surfactants of cationic, anionic and nonionic nature; vegetable oils; mineral oils; waxes; gums; synthetic and natural gelling agents; alkanols; glycols; and polyols. Examples of glycols include, but are not limited to, glycerin, propylene glycol, butylene glycol, pentylene glycol, hexylene glycol, polyethylene glycol, polypropylene glycol, diethylene glycol, triethylene glycol, capryl glycol, glycerol, butanediol and hexanetriol, and copolymers or mixtures thereof. Examples of alkanols include, but are not limited to, those having from about 2 carbon atoms to about 12 carbon atoms (e.g., from about 2 carbon atoms to about 4 carbon atoms), such as isopropanol and ethanol. Examples of polyols include, but are not limited to, those having from about 2 carbon atoms to about 15 carbon atoms (e.g., from about 2 carbon atoms to about 10 carbon atoms) such as propylene glycol. The organic solvents may be present in the carrier in an amount, based upon the total weight of the carrier, of from about 1 percent to about 99.99 percent (e.g., from about 20 percent to about 50 percent). Water may be present in the carrier (prior to use) in an amount, based upon the total weight of the carrier, of from about 5 percent to about 95 percent (e.g., from about 50 percent to about 90 percent). Solutions may contain any suitable amounts of solvent, including from about 40 to about 99.99%. Certain preferred solutions contain from about 50 to about 99.9%, from about 60 to about 99%, from about 70 to about 99%, from about 80 to about 99%, or from about 90 to 99%.

A lotion can be made from such a solution. Lotions typically contain at least one emollient in addition to a solvent. Lotions may comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may contain a simple base of animal, vegetable, or synthetic oils or semi-solid hydrocarbons. An ointment may contain from about 2% to about 10% of an emollient(s) plus from about 0.1% to about 2% of a thickening agent(s).

The compositions useful in the present invention can also be formulated as emulsions. If the carrier is an emulsion, from about 1% to about 10% (e.g., from about 2% to about 5%) of the carrier contains an emulsifier(s). Emulsifiers may be nonionic, anionic or cationic. Lotions and creams can be formulated as emulsions. Typically such lotions contain from 0.5% to about 5% of an emulsifier(s), while such creams would typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The compositions of the present invention can also be formulated into a solid formulation (e.g., a wax-based stick, soap bar composition, powder, or wipe). The composition of the present invention can also be combined with a solid, semi-solid or dissolvable substrate (eg., a wipe, mask, pad, glove or strip).

The compositions of the present invention may further comprise any of a variety of additional cosmetically active agents. Examples of suitable additional active agents include: additional skin lightening agents, darkening agents, anti-acne agents, shine control agents, anti-microbial agents such as anti-yeast agents, anti-fungal, and anti-bacterial agents, anti-inflammatory agents, anti-parasite agents, external analgesics, sunscreens, photo-protectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, firming agents, hydration boosters, efficacy boosters, anti-callous agents, agents for skin conditioning, anti-cellulite agents, fluorides, teeth whitening agents, anti-plaque agents, and plaque-dissolving agents, odor-control agents such as odor masking or pH-changing agents, and the like. Examples of various suitable additional cosmetically acceptable actives include hydroxy acids, benzoyl peroxide, D-panthenol-UV filters such as but not limited to avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, carotenoids, free radical scavengers, spin traps, retinoids and retinoid precursors such as retinol, retinoic acid and retinol palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, amino acids such a proline, vitamins, lactobionic acid, acetyl-coenzyme A, niacin, riboflavin, thiamin, ribose, electron transporters such as NADH and $FADH_2$, and other botanical extracts such as oat, aloe vera, Feverfew, Soy, Shiitake mushroom extracts, and derivatives and mixtures thereof.

In certain preferred embodiments, the compositions of the present invention are skin care compositions that comprise a compound of Formula I and at least one additional skin lightening active agent. Examples of suitable additional skin lightening active agents include, but are not limited to, tyrosinase inhibitors, melanin-inhibiting agents, melanosome transfer inhibiting agents including PAR-2 antagonists, exfoliants, sunscreens, retinoids, antioxidants, Tranexamic acid, skin bleaching agents, allantoin, opacifiers, talcs and silicas, zinc salts, and the like, and other agents as described in Solano et al. Pigment Cell Res. 2006, 19 (550-571). Examples of suitable tyrosinase inhibitors include but, are not limited to, Vitamin C and its derivatives, Vitamin E and its derivatives, Kojic Acid, Arbutin, resorcinols, hydroquinone, Flavones e.g. Licorice flavanoids, Licorice root extract, Mulberry root extract, Dioscorea Coposita root extract, Saxifraga extract and the like, Ellagic acid, Salicylates and derivatives, Glucosamine and derivatives, Fullerene, Hinokitiol, Dioic acid, Acetyl glucosamine, Magnolignane, combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4alkylresorcinols such as 4-butyresorcinol (rucinol), 4-hexylresorcinol, phenylethyl resorcinol, 1(2,4-dihydroxyphenyl)-3-(2,4-dimethoxy-3-methylphenyl)-Propane and the like and natural extracts enriched in resorcinols. Examples of salicylates include, but are not limited to, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative. In more preferred embodiments, the tyrosinase inhibitor comprises Phenylethyl resorcinol, 4-hexyl resorcinol, or ascorbyl-2-glucoside.

Examples of suitable melanin-degradation agents include, but are not limited to, peroxides and enzymes such as peroxidases and ligninases. In certain preferred embodiments, the melanin-inhibiting agents include a peroxide or a ligninase.

Examples of suitable melanosome transfer inhibiting agents including PAR-2 antagonists such as soy trypsin inhibitor or Bowman-Birk Inhibitor, Vitamin B3 and derivatives such as Niacinamide, Essential soy, Whole Soy, Soy extract. In certain preferred embodiments, the melanosome transfer inhibiting agents includes a soy extract or niacinamide.

Examples of exfoliants include, but are not limited to, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid, and mechanical exfoliation such as microdermabrasion. In certain preferred embodiments, the exfoliant include glycolic acid or salicylic acid.

Examples of sunscreens include, but are not limited to, avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate 0 (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, and the like.

Examples of retinoids include, but are not limited to, retinol, retinaldehyde, retinoic acid, retinyl palmitate, isotretinoin, tazarotene, bexarotene and Adapalene. In certain preferred embodiments, the retinoid is retinol.

Examples of antioxidants include, but are not limited to, water-soluble antioxidants such as sulfhydryl compounds and their derivatives (e.g., sodium metabisulfite and N-acetyl-cysteine, glutathione), lipoic acid and dihydrolipoic acid, stilbenoids such as resveratrol and derivatives, lactoferrin, and ascorbic acid and ascorbic acid derivatives (e.g., ascobyl-2-glucoside, ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, feverfew, parthenolide-free feverfew, oat extracts, pomelo extract, wheat germ extract, Hesperidin, Grape extract, Portulaca extract, Licochalcone, chalcone, 2,2'-dihydroxy chalcone, Primula extract, propolis, and the like.

The additional cosmetically active agent may be present in a composition in any suitable amount, for example, in an amount of from about 0.0001% to about 20% by weight of the composition, e.g., about 0.001% to about 10% such as about 0.01% to about 5%. In certain preferred embodiments, in an amount of 0.1% to 5% and in other preferred embodiments from 1% to 2%.

A variety of other materials may also be present in the compositions of the present invention. These include, for example, chelating agents, humectants, opacifiers, conditioners, preservatives, fragrances and the like. The compositions may include surfactants, for example, those selected from the group consisting of anionic, non-ionics, amphoteric, cationic, or a combination of two or more thereof.

In certain preferred embodiments, the present invention comprises applying a compound or composition of the invention via a substrate comprising such material. Any suitable substrate may be used in the present invention. Examples of suitable substrates and substrate materials are disclosed, for example, in U.S. Published Application Nos.

2005/0226834 and 2009/0241242 which are incorporated herein by reference in their entirety.

In certain preferred embodiments, the substrate is a wipe or a facial mask. Preferably, such embodiments comprise a water-insoluble substrate as such is defined in the cited references above. For certain embodiments, the water-insoluble substrate may have a size and shape such that it covers the face of a human user to facilitate placing the water-insoluble substrate about the face of the user as a mask substrate. For example, the water-insoluble mask substrate may have openings for a mouth, nose, and/or eyes of the user. Alternatively, the water-insoluble substrate may have no such openings. Such a configuration without openings may be useful for embodiments of the invention in which the water-insoluble substrate is intended to be draped over a non-facial expanse of skin or if the water-insoluble substrate is intended to be used as wipe. The water-insoluble substrate may have various shapes, such as an angular shape (e.g., rectangular) or an arcuate shape such as circular or oval.

In one embodiment of the invention, the product includes a plurality of water-insoluble substrates of different shapes. In one embodiment of the invention, the product includes a first water-insoluble substrate and a second water-insoluble substrate. The first water-insoluble substrate is shaped for application onto the forehead and the second water-insoluble substrate is shaped for application proximate to the mouth, such as areas above and/or below the lips, the chin, and/or the cheeks. In one embodiment of the invention, the first water-insoluble substrate is also applied to the nose region of the face. The first water-insoluble substrate may have a surface area of from about 100 $cm^2$ to about 200 $cm^2$, such as from about 120 $cm^2$ to about 160 $cm^2$ and the second water-insoluble substrate has a surface area of from about 100 $cm^2$ to about 300 $cm^2$, such as from about 150 $cm^2$ to about 250 $cm^2$. In one embodiment of the invention, the water-insoluble substrate has a low stiffness such that it may, for example, readily drape over or conform to the face or other body parts of the user.

The present invention may comprise application to any skin in need of treatment on the human body. For example, application may be made to any one or more of the skin of the face, neck, chest, back, arms, axilla, hands and/or legs. In certain preferred embodiments, the method comprises applying a compound of Formula I to skin of the face.

Any suitable method of applying the extract to the skin in need may be used in accord with the present invention. For example, the extract may be applied directly from a package to the skin in need, by hand to the skin in need, or may be transferred from a substrate such as a wipe or mask, or a combination of two or more thereof. In other embodiments, the extract may be applied via a dropper, tube, roller, spray, patch or added to a bath or otherwise to water to be applied to the skin, and the like.

In certain embodiments, the methods of the present invention further comprise the step of leaving the compound of Formula I in contact with the skin for period of time. For example, in certain preferred embodiments after application, the compound is left in contact with the skin for a period of about 15 minutes or greater. In certain more preferred embodiments, the extract is left in contact with the skin for about 20 minutes or greater, more preferably about 1 hour or greater.

In certain embodiments, the method of the present invention comprises a regimen comprising applying the compound of Formula I to skin multiple times over a selected period of time. For example, in certain embodiments, the present invention provides a method of skin lightening comprising applying to skin in need of skin lightening a composition comprising a compound of Formula I once or twice daily for at least 12 weeks, preferably at least 8 weeks and more preferably for at least 2 weeks.

In certain preferred embodiments, the methods of the present invention comprise applying at least two different compositions or products comprising compound of Formula I to the skin. For example, the methods may comprise applying a first composition comprising compound of Formula I to skin in need of skin lightening followed by applying a second composition comprising compound of Formula I, but that is otherwise different from the first composition, to the skin in need of skin lightening. In certain preferred embodiments, the first and second composition may be independently selected from the group consisting of lotions, cleansers, masks, wipes, creams, serums, gels, and the like. In certain preferred embodiments, at least one of the first and second compositions is a cleanser, lotion, cream, essence, or serum and the other is a facial mask or wipe. In certain other preferred embodiments, at least one of the first and second compositions is a cleanser and the other is a lotion or cream.

In certain other preferred embodiments, the method comprises applying at least three products comprising compound of Formula I to skin in need of skin lightening. Preferably such three products are selected from the group consisting of cleansers, lotions, creams, essences, and facial masks.

EXAMPLES

The following test methods were used in the Examples:
Melanin Synthesis Inhibition Test Control samples of B16(F10) murine melanoma cells were prepared and harvested as indicated below, but without addition of any test sample and without exposure to UVB (untreated control). Other control samples were prepared and harvested as indicated below without addition of test sample and exposed to UVB as described below (treated control). One or more samples of B16(F10) cells were prepared and each pre-treated with a test sample (e.g. E1) followed by UVB exposure as described below. Upon treatment, UVB stimulated melanogenesis in the cells and test compounds were evaluated based on their ability to inhibit or slow down the rate of melanogenesis. The cells were lysed for protein measurement at 595 nm and melanin content at 470 nm. The potency of the test compounds were determined by comparing the % inhibition achieved by the test compounds against the treated control.

Testing Procedure:

On a first day, murine melanoma B16(F10) cells were seeded in 60 mm plates with a density of ~1 million cells per plate and incubated for 48 hrs at 37° C., 5% $CO_2$. On day 2, the cells with a confluency rate of 90-100% were treated with test compound at a predetermined concentration (e.g. 25 µg/mL) for two hours (for test compound samples only) followed by exposure to UVB 20 $mJ/cm^2$ (for test samples and treated control). The cells were harvested on day 3 (24 h post UVB irradiation for test samples and treated control) and lysed in protein lysis buffer (50 mM Tris, pH 8, 2 mM EDTA, 150 mM NaCl, and 1% Triton X 100—a nonionic surfactant purchased from BioRad Cat. #: 161-0407), and centrifuged. The resulting supernatant was mixed well with a protein dye assay (Bio-rad protein assay reagent) and a spectrophotometer (Molecular Devices VERSAmax) was used to determine the optical density (protein assay OD) of the sample at 595 nm. The cell pellet remaining after removal of the supernatant was dissolved in alkaline DMSO buffer, and the resulting solution used for melanin absorbance assay at 470 nm to determine melanin assay OD.

Three samples each of the untreated control, treated control, and each test sample were made and the Melanin and Protein OD measured for each. The normalized melanin for each untreated control (3 samples), treated control (3 samples) and test sample (3 samples for each test compound) was calculated via the following equation:

Normalized Melanin=melanin assay OD/protein assay OD.

The average normalized Melanin of the untreated controls was calculated (sum of the three calculated values/3), and the average normalized Melanin of the treated controls similarly calculated.

The Induction value of the Control was calculated via the equation:

Induction value of Control=average normalized Melanin of treated control−average normalized Melanin of untreated control.

The Induction value with each test sample is then calculated via the equation:

Induction value with Test Sample=normalized Melanin of the test sample−average normalized Melanin of untreated control.

The Inhibition % for each test sample is then calculated via the equation:

100×[(Induction value of Control−Induction value with Test Sample)/Induction value of Control].

The average Inhibition % is calculated as the sum of the three resulting Inhibition % values for each test sample divided by three.

The calculation sequence for % inhibition are explained by a theoretical example, see the following table.

| | |
|---|---|
| Average normalized melanin Untreated control | 0.98 |
| Average normalized melanin UVB treated control | 2.56 |
| Induction value of control | 2.56 − 0.98 = 1.58 |
| Average normalized melanin Test sample | 1.04 |
| Induction value with Test sample | 1.04 − 0.98 = 0.06 |
| Inhibition % for Test sample | [(1.58 − 0.06)/1.58] × 100 = 96.20% |

Tyrosinase Inhibition Test

Tyrosinase inhibition activity was measured with two different test protocols. In one experiment tyrosinase protein enzyme was obtained from B16(F10) mouse cells. In another experiment commercially available mushroom tyrosinase enzyme was used. The detail procedures and the data obtained are as follows Tyrosinase protein enzyme was obtained from B16(F10) mouse cells. The B16(F10) murine melanoma cells from 10 confluent T-175 flasks were lysed using 5 ml of lysis buffer (50 mM Tris, pH 8, 2 mM EDTA, 150 mM NaCl, 1% Triton X and 1× protease inhibitor cocktail). The lysate was kept on ice for 30 minutes, with interval vortexing before it was spun at 21,000 g for 10 minutes at 4° C. Protein concentration in the supernatant was determined using Bradford assay. The supernatant was aliquot to 500 μL per eppendorf tube and stored at −80° C. for up to 2 weeks.

For a typical assay, 50 μg of protein lysate was incubated with the test compound at 200 μg/mL before the addition of freshly prepared 10 mM L-DOPA in 50 mM Phosphate buffer, pH 6.8 (reaction volume=100 mL). The samples were incubated in the 37° C. $CO_2$ incubator for 3 hours before the final OD was measured. Kojic Acid (100 μg/mL) is used as positive control. Control reference (sample+Buffer+L-DOPA) for each sample was included.

L-Tyrosine Tyrosinase Inhibition: For L-tyrosine assay, 6-8 IU of mushroom tyrosinase (Sigma T3824) was incubated with the test compound at 200 μg/mL before the addition of freshly prepared 1 mM L-tyrosine in 50 mM Phosphate buffer, pH 6.8 (reaction volume=120 mL). The samples were incubated at 37° C. for 30 minutes before the final OD was measured. Kojic acid (100 μg/ml) and Sym-White 377 (0.001%) were used as positive controls. Control reference (sample+Buffer+L-DOPA) for each sample was included.

Skin Epidermal Equivalents Model as a Skin Lightening Test (ΔL)

Skin epidermal equivalent tissues are available commercially from MatTek's MelanoDerm™ System and were used for the following tests. MatTek's MelanoDerm™ System consists of normal, human-derived epidermal keratinocytes (NHEK) and melanocytes (NHM) which have been cultured to form a multilayered, highly differentiated model of the human epidermis. Specifically, MEL-300-B tissues, each 9 mm in diameter were used in the following tests.

The test materials prepared in an appropriate vehicle and tested concentrations were applied topically to the skin model daily and the experiment lasted for 8 days. Measurement was taken on day 9.

The macroscopic and microscopic visual tissue darkening end points were measured by taking pictures with a digital camera. The Degree of Lightness for each tissue (L-Value) was measured using a spectrophotometer (Konica Minolta CM-2600d). The ΔL (degree of lightness as compared to control) for each test sample is calculated as per following formula:

ΔL=L-value of treated sample−L-value of control sample.

According to certain preferred embodiments, the compositions of the present invention are effective to achieve a ΔL in accord with this test of greater than zero. More preferably, the compositions of the present invention are effective to achieve a ΔL of about 0.5 or greater, more preferably about 1 or greater. In certain more preferred embodiments, the compositions of the present invention are effective to achieve a ΔL of about 2 or greater, more preferably about 3 or greater, and more preferably about 4 or greater.

Cell Viability Test

Cell Viability of the tissue during experiment was evaluated using the MTT assay described as follows. The MTT Tissue Viability Assay is a colorimetric assay system that measures the reduction of a yellow Methylthiazolyldiphenyl-tetrazolium bromide (MTT) into an insoluble purple product by the mitochondria of viable cells.

The skin epidermal tissues used previously to determine degree of lightness for each test material and of untreated tissues were used to determine percent viable cells remaining at the end of the experiment. The skin epidermal tissues after degree of lightness test were incubated with MTT reagent for 3 h. After incubation extraction buffer is added to lyse the cells and allowed to continue overnight. Samples are read using a plate reader at a wavelength of 570 nm and compared against untreated control and expressed in % Cell Viability as of control. A reduction of ≥30% cell viability as of control is considered as a significant indication of cell cytotoxicity caused by the test materials. The amount of purple color produced is directly proportional to the number of viable cells.

The NF-κB Inhibition Assay

The NF-κB promoter assay is conducted as follows: rat cardiac myoblasts H9c2 cells were purchased from ATCC (Manassas, Va.). Cultures were maintained in Dulbecco's modified Eagle's medium (DMEM, Invitrogen Life Technologies, Carlsbad, Calif.) supplemented with 10% fetal bovine serum, 100 units/ml penicillin, and 50 µg/ml streptomycin (Invitrogen life technologies, Carlsbad, Calif.). Typically, $1\times10^4$ cells grown in 96-well plates were transiently transfected with 0.45 µg total DNA per well using Lipofectamine 2000 (Invitrogen life technologies, Carlsbad, Calif.). In all transfections, a construct with the thymidine kinase promoter and the Renilla luciferase reporter gene (pRL-TK, Promega, Madison Wis.) was included as an internal control in addition to the luciferase promoter. One day after transfection, cells were treated with the extracts at indicated concentrations and stimulated with 100 ng/mL of Tumor Necrosis Factor-α (TNFα, Sigma-Aldrich, St Louis, Mo.) for approximately 24 hours before they were lysed for luciferase assays, using Dual-Luciferase Reporter System from Promega (Madison, Wis.), following manufacturer's protocol. Briefly, the firefly luciferase activity was measured first (representing NF-κB promoter activity), followed by the renilla luciferase (internal control), using luminometer LMAX, from Molecular Devices (Sunnyvale, Calif.). The ratio of these two luciferase activities (RLU) was used to evaluate the activity of each promoter.

$$\text{NF-κB Inhibition} = [1-(\text{RLU}_{sample}/\text{RLU}_{control})]*100$$

where $\text{RLU}_{sample}$ and $\text{RLU}_{control}$ are the normalized luciferase activity ratios of the sample and control, respectively.

Example 1

Preparation of *Acronychia acidula* Fruit Extract (E1)

Extract (E1)—A typical extraction process is described here as an example. 500 gm of freeze-dried fruits of *Acronychia acidula* were sliced into approximately 5 mm cubes and soaked with 5 L of ethanol at a ratio of 1:10 (raw material to solvent) and stirred at room temperature for 12 hours. The suspension was then filtered and the filtrate was concentrated under low pressure to afford a concentrate. The concentrate then further dried by freeze-drying methods to obtain 325 gm of residual material called crude extract (65% yield). A sample of the crude extract, 200 gm, was taken up in 1 L ethanol and stirred at room temperature overnight. The mixture was filtered and dried at reduced pressure and at low temperature. A gummy material Example 2

Melanogenesis Inhibition for *Acronychia acidula* Fruit Extract (E1)

The extract E1 was tested for Melanogenesis Inhibition in accord with the Melanin Synthesis Inhibition Test as described above. The results are shown in Table 1 below.

TABLE 1

Melanogenesis Inhibition of *Acronychia acidula* fruit Extract

| Test Description | Extract Conc. (µg/mL) | Inhibition (%) |
|---|---|---|
| UV-induced Melanogenesis | 20 | 84 |
| B16(F10) | 200 | 122 |

Example 3

Tyrosinase Inhibition for *Acronychia acidula* Fruit Extract (E1)

The following example demonstrates the Tyrosinase inhibition activity of E1. The extracts E1 was tested at the concentrations indicated in Table 2 for Tyrosinase inhibition in accord with the Tyrosinase Inhibition tests described above. The results are shown in Table 2 below.

TABLE 2

Tyrosinase Inhibition of *Acronychia acidula* fruit Extract

| Test Description | Extract Conc. (µg/mL) | Inhibition (%) |
|---|---|---|
| Tyrosinase B16(F10) | 200 | 6 |
| Mushroom tyrosinase | 200 | 0 |

Example 4

Skin Lightening Activity for *Acronychia acidula* Fruit Extract (E1)

The following example illustrates the skin lightening properties of Extract E1. The extract was tested for skin lightening (ΔL) in accord with the Skin Epidermal Equivalents Model as described above. Cytotoxicity potential was determined by MTT assay for extract E1 and calculated as % reduction of cell viability as compared to control, wherein >30% reduction of cell viability constitutes significant cytotoxicity issues. The results are shown in Table 3 below.

TABLE 3

Skin lightening activity (ΔL) of extracts

| Extract (concentration (%)) | ΔL | Melanin Reduction (%) |
|---|---|---|
| E1 (1%)* | 5.8 | 26 |

*No cell cytotoxicity was observed.

Example 5

Fractionation of First Extract (E1) of *Acronychia acidula* Fruit Extract 0.1 gm of first extract (E1) was loaded on 2 gm of reverse phase C18 silica gel and eluted sequentially with 100 mL of pure water, 100 mL of 50% aq. methanol, and then with 100 mL of pure methanol producing fractions 1-3 respectively. All three fractions were dried under reduced pressure yielding 78 mg (78%) material from fraction 1 (F1), 19 mg (19%) material from fraction 2 (F2) and small quantities of material from fraction 3 (<3%).

Example 6

Skin Lightening Activity for *Acronychia acidula* Fruit Fractions F1 & F2

The fruit factions (F1 & F2) of *Acronychia acidula* were tested for skin lightening (ΔL) in accord with the Skin Epidermal Equivalents Model as described above at concentrations given in Table 4. The results are shown in Table 4 below.

TABLE 4

Skin lightening activity (ΔL) of *Acronychia acidula* fruit fractions

| Fraction | Concentration (%) | Skin Lightening (ΔL Value) |
|---|---|---|
| F1 | 2 | 1 |
| F2 | 2 | 4.5 |

Example 7

Purification of Fraction F2 to Generate Pure Major Component (M-1)

The major compound from *Acronychia acidula* fruit fraction F2 was isolated by flash chromatography over silica gel and identified as 3-(4-Farnesyloxyphenyl)propionic acid (M-1) through H-NMR and high resolution MS. Based on molecular weight of 370.54, molecular formula for M-1 was found to be $C_{24}H_{34}O_3$. Multi-dimensional NMR spectroscopy confirmed the identity of M-1. The natural abundance of M-1 in *Acronychia acidula* fruit extract is determined and found to be about 19%. Additionally, five minor compounds were also tentatively identified but were not purified. Two of them are new compounds and found to be the analogs of M-1 with an additional hydroxyl group in one case and a methoxyl group in another. Ethyl ester versions of these compounds were also detected and expected to be the artifacts of extraction method. Total natural abundance of all these compounds was determined and found to be about 20%. Moreover spectroscopic data were analyzed to determine the presence of chemicals with nitrogen, prenylated acetophenone or simple acetophenone functionalities and found none.

Example 8

Skin Lightening Activity of 3-(4-farnesyloxyphenyl)propionic Acid (M-1)

3-(4-Farnesyloxyphenyl)propionic acid (M-1) isolated as indicated above was tested for skin lightening (ΔL) in accord with the Skin Epidermal Equivalents Model as described above. First extract (E1) was also tested at the same concentration for reference purpose. Component M-1 exhibited skin lightening efficacy equal to first extract E1. The results are shown in Table 5 below.

TABLE 5

Skin lightening activity (ΔL) of *Acronychia acidula* major component

| Fraction | Concentration (%) | Skin Lightening (ΔL Value) |
|---|---|---|
| M-1 | 0.5 | 1.2 |
| E1 | 0.5 | 1.0 |

Example 9

Preparation of Composition

A product formula in cream with an extract in accord with the present invention is given in the following Table 6.

TABLE 6

Product formulation

| Item # | Ingredient/Function | Trade/INCI Name | % Weight |
|---|---|---|---|
| 1. | Purified Water | Water | Balance |
| 2. | EDTA BD | Disodium EDTA | 0.10 |
| 3. | Emulsifiers | Pemulen TR-1, Brij72, Brij 721, Lanette 22, Amphisol K, Simulgel EG | 4.90 |
| 4. | Thickeners | Carbopol Ultrez 20, Xanthan gum 180 | 0.20 |
| 5. | Humectants | Butylene Glycol, Glycerin | 9.00 |
| 6. | Skin Conditioning Agent | Prodew 300, Cetiol SB-45, Edenor ST 1 MY, Miglyol 812N, Finsolve TN, DC 200 cps, DC 345 Fluid, DC 1403, SP-500 | 15.75 |
| 7. | *Portulaca* Extract | *Portulaca oleracea* extract, Butylene Glycol, Water | 2.00 |
| 8. | Dipotassium Glycyrrhizate | Dipotassium Glycyrrhizate | 0.25 |
| 9. | Lemon Aspen extract | *Acronychia acidula* fruit extract | 1.00 |
| 10. | Preservatives | Methyl paraben, Ethyl paraben, Propyl paraben | 0.60 |
| 11. | Neutralizing Base | Sodium Hydroxide | As per need |
| 12. | UV Filter | Titanium Dioxide | 0.20 |
| 13. | Fragrances | Fragrance for Memory 161FF | 0.20 |
| 14. | Chlorohexidine Digluconate 20% | Chlorohexidine Digluconate | 0.25 |
| 15. | Hydrolite-5 | Pentylene Glycol | 1.00 |
| 16. | Vitamin E Acetate | Tocopherol acetate | 0.25 |
| 17. | Alpha Bisabolol | Bisabolol | 0.25 |

The ingredients are mixed as per standard procedures. A brief general procedure is described here for guidance.

Premix A: Dissolve Lemon aspen extract in butylene glycol and water.

Premix B: Mix Glycerin and Xanthan 180 until a uniform mixture is achieved.

Premix C: Disperse SP 500 in Butylene glycol

Water Phase:
  Add water into the vessel, begin agitation, add EDTA BD and mix until uniform.
  Sprinkle in Pemulen TR-1 and Carbopol Ultrez 20 and mix until a translucent mixture is obtained.
  Add Prodew 300, Butylene glycol, and Xantural Premix B until uniform.
  Start heating to 80-83° C.
  At 70-75° C., add methyl paraben and mix until uniform.
  At 80° C., add sodium hydroxide to neutralize the water phase, hold temperature until phasing Oil Phase:
  Mix Miglyol 815, Finsolve TN, Lanette 22, Edenor ST1 MY, Brij 721, Cetiol SB45, Ethyl paraben, Propyl paraben, and heat to 80° C. Check that a clear melt is achieved before sprinkling in UV Titan M262 and mix for 20 minutes. At 80° C., add Amphisol K and mix until uniformly dispersed. Hold the temperature at 80-83° C. until phasing.

Phasing:

Add oil phase to water phase under homogenization
Add Simulgel EG and mix until uniform. Do not proceed until thickening effect is observed.
Start cooling to 60-65° C.
At 60-65° C., slowly add Premix A.
At 55-60° C., add DC 200 50 cst, DC 345 and DC 1403 and mix until uniform.
At 45° C., add Premix C.
At below 35° C., add Hydrolite 5, Chlorohexidine digluconate, Portulaca extract, Alpha Bisabolol, Vitamin E acetate, Fragrance, and mix until uniform and homogenize the batch for 5 minutes.

Example 10

Preparation of Composition

A product formula with an extract in accord with the present invention is given in the following Table 7.

TABLE 7

Product formulation

| Item # | INCI Name | Trade Name | % Weight |
|---|---|---|---|
| 1. | Water | Purified Water | 71.59 |
| 2. | Xanthan Gum | Keltrol CG | 0.16 |
| 3. | Edetate Disodium | Versene NA | 0.15 |
| 4. | White Petrolatum | Perfecta | 5 |
| 5. | Medium Chain Triglyceride | Labrafac CC | 0.75 |
| 6. | Glycerin | Glycerol | 5.50 |
| 7. | Ricinus Communis seed oil | Castor Oil | 1.8 |
| 8. | Cetyl Alcohol, NF | Lanette 16 | 2.2 |
| 9. | Emulsifying Wax, NF | PolaWax, NF | 1.5 |
| 10. | Cocoa Butter | Cocoa Butter, NF | 2 |
| 11. | Glyceryl Stearate SE | Glyceryl Stearate SE | 3.00 |
| 12. | Glyceryl Stearate/PEG 100 Stearate | Lexemul 561 | 5.00 |
| 13. | Diazolidinyl Urea | Germall II | 0.25 |
| 14. | Acronychia acidula (1% active) | Lemon aspen extract | 1.00 |
| 15. | 3-Iodo-2-propynyl butyl carbamate | Glycacil L | 0.1 |

Water Phase:
Step 1. Charge purified water into the main container at a temperature of 20-40° C.
Step 2. Add the Xanthan Gum NF to the main container. *Note: If Xanthan Gum is lumpy use 30 mesh screen.
Step 3. Rinse the wall of the main container with Purified Water to remove any Xanthan Gum from the walls.
Step 4. Mix the batch for 15-25 minutes. Check hydration of the gum and proceed if acceptable.
Step 5. Continue mixing and add Glycerin USP Special and Edetate Disodium USP
Step 6. Start heating the batch to 65° C. (63-67° C.) and continue mixing.

Oil Phase:
Step 1. Into a clean suitable phase container add the following chemicals in this order: Medium Chain Triglycerides, Castor Oil, Cocoa Butter, and Premelted Petrolatum USP.
Step 2. Set the oil phase temperature to 65° C. (63-67° C.) and start mixing at medium speed.
Step 3. While heating the batch to 65° C., add the following chemicals in this order, allowing each to dissolve before adding the next: Glyceryl Stearate SE, Cetyl Alcohol, Emulsifying Wax, and Glyceryl Stearate.
Step 4. When the temperature reaches 65° C. (63-67° C.) mix for 15-25 minutes.

Phasing:
Step 1. When both phases are homogenous and at a temperature of 63-67° C., transfer the oil phase to the water phase while mixing the water phase at medium speed.
Step 2. When transfer is completed, rinse oil phase tank with Purified Water. Heat rinsings to 63-67° C. and add it to the main container.
Step 3. Mix the batch for 10-20 minutes.
Step 4. Turn on cooling and cool the batch to 40° C. (38-42° C.).
Step 5. When temperature is 48-50° C. increase mixing speed to medium-high.
Step 6. Add Acronychia acidula fruit extract (1% active)
Step 7. When temperature is at 44° C. or lower, add the Diazolidinyl Urea Premix.
Step 8. Add 3-Iodo-2-propynyl butyl carbamate.
Step 9. Mix the batch for 5-10 minutes.
Step 10. If required, QS the batch with Purified Water.
Step 11. Continue mixing and start cooling of batch to 32-34° C.
Step 12. When the batch reaches 33° C. (32-34° C.), turn off mixing and stop cooling.

Diazolidinyl Urea (Germall II) Premix
Step 1. Into a stainless steel premix tank add Purified Water.
Step 2. Start mixing the water and add Diazolidinyl Urea.
Step 3. Mix for an additional 10-20 minutes to dissolve completely.
Step 4. Hold the premix for addition to the batch.

What is claimed is:

1. A method of lightening skin comprising applying to skin in need of skin lightening a cosmetic composition comprising an ethanol extract of a plant of the genus Acronychia in an amount sufficient to cause lightening of the skin, and a cosmetically acceptable carrier;

wherein said extract contains at least about 5% by weight of a compound of Formula I:

$$\text{(I)}$$

wherein:

$R_1$ is selected from the group consisting of $C_1$-$C_{20}$ alkyl, $C_2$-$C_{20}$ alkenyl, $C_2$-$C_{20}$ alkynyl, and $C_3$-$C_8$ cycloalkyl or aryl;

$R_2$ is selected from the group consisting of hydrogen, hydroxyl, $C_1$-$C_6$ alkyl, $C_2$-$C_6$ alkenyl, $C_2$-$C_6$ alkynyl, $C_3$-$C_8$ cycloalkyl or aryl, $-OC_1$-$C_6$ alkyl, $-OC_2$-$C_6$ alkenyl, $-SC_2$-$C_6$ alkenyl, $-SC_2$-$C_6$ alkynyl, $-SC_3$-$C_8$ cycloalkyl or aryl, $-NR_4C_1$-$C_6$ alkyl, $-NR_4C_2$-$C_6$ alkenyl, $-NR_4C_2$-$C_6$ alkynyl, and $-NR_4C_3$-$C_8$ cycloalkyl or aryl;

$R_3$ is selected from —$CO_2H$, —$CO_2R_4$ or an isosteric equivalent of a carboxy group, wherein $R_4$ is $C_1$-$C_6$ alkyl, $C_2$-$C_6$ alkenyl, $C_3$-$C_8$ cycloalkyl or aryl; and Y is —($CH_2$-$CH_2$)—, —(CH=CH)—, or —(C≡C)—; or a cosmetically acceptable salt thereof and said composition comprises from about 0.001 to about 10% of compound of Formula I.

2. The method of claim 1 wherein:

$R_1$ is selected from the group consisting of $C_5$-$C_{16}$ alkyl, $C_5$-$C_{16}$ alkenyl, and $C_5$-$C_{16}$ alkynyl;

$R_2$ is selected from the group consisting of hydrogen, hydroxyl, —$OC_1$-$C_6$ alkyl, —$OC_2$-$C_6$ alkenyl, —$OC_2$-$C_6$ alkynyl, —$OC_3$-$C_8$ cycloalkyl;

$R_3$ is selected from —$CO_2H$, —$CO_2R_4$ wherein $R_4$ is $C_1$-$C_6$ alkyl, or an isosteric equivalent of a carboxy group; and Y is —($CH_2$-$CH_2$)— or —(CH=CH)—.

3. The method of claim 2, wherein:

$R_1$ is selected from the group consisting of $C_5$-$C_{16}$ alkenyl; and $R_2$ is selected from the group consisting of hydrogen or —$OC_1$-$C_3$ alkyl.

4. The method of claim 2, wherein the compound of Formula I is selected from the group consisting of 3-(4-farnesyloxyphenyl)-propionic acid, 3-(4-farnesyloxy-3-hydroxyphenyl)-propionic acid, 3-(4-farnesyloxy-3-methoxyphenyl)-propionic acid, alkylesters thereof, ethyl esters thereof, and combinations of two or more thereof.

5. The method of claim 4, wherein the compound of Formula I comprises 3-(4-farnesyloxyphenyl)-propionic acid and 3-(4-farnesyloxy-3-methoxyphenyl)-propionic acid.

6. The method of claim 5, wherein the compound of Formula I comprises 3-(4-farnesyloxyphenyl)-propionic acid.

7. The method of claim 1, wherein the composition comprises from about 0.01 to about 1% of compound of Formula I.

8. The method of claim 1, wherein said botanical extract is an extract of *Acronychia acidula*.

9. The method of claim 1, wherein said composition further comprises at least one additional skin lightening active agent.

10. The method of claim 1, wherein said skin in need of skin lightening is skin on a human face.

11. The method of claim 10, wherein said composition is applied using a facial mask comprising a mask substrate.

12. The method of claim 1, wherein said extract is free from acetophenones.

13. The method of claim 12, wherein said extract is free from prenylated acetophenones.

14. The method of claim 13, wherein said extract is free from acrovestone and its analogs.

15. The method of claim 1, wherein said extract is obtained from the fruit of the *Acronychia*.

16. The method of claim 1, wherein said extract of a plant of the genus *Acronychia* is made from a species selected from the group consisting of: *aberrans, acidula, acronychioides, acuminate, baeuerlenii, chooreechillum, crassipetala, eungellensis, imperforate, laevis, laurifolia, littoralis, oblongifolia, octandra, parviflora, pauciflora, pubescens, Batavia Downs, suberosa, vestita, wilcoxiana*, and combinations of two or more thereof.

17. The method of claim 1, wherein said composition further comprises at least one of pentylene glycol, butylene glycol, propylene glycol, glycerin or combinations.

18. The method of claim 14, wherein said composition further comprises at least one of pentylene glycol, butylene glycol, propylene glycol, glycerin or combinations thereof.

19. A method of lightening skin comprising applying to skin in need of skin lightening a cosmetic composition comprising an ethanol extract of a plant of the genus *Acronychia* in an amount sufficient to cause lightening of the skin, and a cosmetically acceptable carrier;

wherein said extract contains at least about 20% by weight of 3-(4-farnesyloxyphenyl)-propionic acid, said composition comprises from about 0.001 to about 10% of 3-(4-farnesyloxyphenyl)-propionic acid; and wherein said extract is free from acrovestone and its analogs.

* * * * *